United States Patent [19]

Hess

[11] 4,223,160
[45] Sep. 16, 1980

[54] REACTION OF OXIRANE COMPOUNDS WITH CARBOXYLIC ACIDS

[75] Inventor: Lawrence G. Hess, Charleston, W. Va.

[73] Assignee: Union Carbide Corporation, New York, N.Y.

[21] Appl. No.: 24,018

[22] Filed: Mar. 26, 1979

[51] Int. Cl.$^2$ ............... C07C 69/02; C07C 69/54; C07C 69/74; C07C 69/76

[52] U.S. Cl. .................................. 560/209; 560/1; 560/112; 560/122; 560/240; 560/254; 560/263; 560/264; 252/441; 252/461; 252/472

[58] Field of Search ............... 560/209, 200, 93, 240, 560/1, 122, 112, 129, 263, 254, 264; 252/472, 461, 441

[56] References Cited

U.S. PATENT DOCUMENTS

| | | | |
|---|---|---|---|
| 3,150,167 | 9/1964 | Wright et al. | 560/209 |
| 3,360,585 | 12/1967 | Winnick | 260/566 A |
| 3,466,320 | 9/1969 | Hargis | 252/461 |
| 3,639,449 | 2/1972 | Kunugi | 252/472 |
| 3,817,931 | 6/1974 | Brooks et al. | 252/463 |
| 3,968,135 | 7/1976 | Steele et al. | 560/209 |
| 4,069,242 | 1/1978 | Gurgiolo | 560/209 |
| 4,118,426 | 10/1978 | Holy et al. | 560/209 |

OTHER PUBLICATIONS

Sato, Masayuki et al. "Epoxy Compounds" Japanese Patent 75-00,007 (See Chemical Abstracts vol. 83 (1975) #43, 171n.

*Primary Examiner*—Natalie Trousof
*Assistant Examiner*—L. Hendriksen
*Attorney, Agent, or Firm*—Stanley Ktorides

[57] ABSTRACT

Niobium and ruthenium salts are employed as catalyst in the reaction of oxirane compounds with carboxylic acids. The acrylate esters produced can be used in photocurable compositions.

11 Claims, No Drawings

REACTION OF OXIRANE COMPOUNDS WITH CARBOXYLIC ACIDS

BACKGROUND OF THE INVENTION

Photocurable compositions have found wide use in many industrial and commercial applications such as in textiles, adhesive, sealants, paints and other coatings because they cure rapidly and do not contain volatile solvents to any large extent as well as having in many cases advantages in flow properties, pigment binding properties and gloss retention. Among the monomers used in the production of photocurable compositions are the hydroxyalkyl acrylate and hydroxyalkyl methacrylate esters, which are generally produced by the reaction of alkylene oxides with acrylic or methacrylic acid. This reaction is well known to those skilled in the art.

It is of great importance that by-product formation during the preparation of hydroxyalkyl acrylates and methacrylates from alkylene oxide and acrylic or methacrylic acid be minimized in order to avoid, to as great an extent as possible, polymerization problems during distillation of the crude products to isolate the refined material. In particular, the formation of the diacrylic and dimethacrylic esters of the alkylene glycols should be avoided due to the known poor stability of the diacrylates and dimethacrylates toward polymerization which is primarily responsible for instability of crude products. Undesirable by-product formation usually increases with temperature and residence time.

In order to increase the efficiency of this very useful reaction, those skilled in the art have sought catalysts which would promote the reaction at lower temperatures and shorter residence times in attempts to minimize by-product formation. Because of the economic importance of the reaction of alkylene oxides with carboxylic acids such as acrylic and methacrylic acid, there continues an intense search for novel compounds which can effectively and efficiently catalyze this reaction. Any such catalyst would be of great importance.

SUMMARY OF THE INVENTION

It has now been found that niobium and ruthenium compounds can be used as catalysts for the reaction of oxirane compounds with carboxylic acids to efficiently produce hydroxyalkyl carboxylates. Specifically, these catalysts can be employed in the synthesis of hydroxyethyl and hydroxypropyl acrylates and methacrylates, which are useful monomers in the production of photocurable compounds.

DESCRIPTION OF THE INVENTION

In the process of this invention, niobium and ruthenium compounds are employed as catalysts in the reaction of oxirane compounds with carboxylic acids to form hydroxyalkyl esters.

The niobium and ruthenium compounds useful as catalysts in the process of this invention can be either organic or inorganic compounds of these metals. Such compounds are well known to those skilled in the art and many are readily available. Among the known compounds that can be used and illustrative thereof one can mention niobium oxalate, niobium pentachloride, niobium acetate, niobium octoate, niobium pentafluoride, ruthenium trichloride, ruthenium tetrachloride, ruthenium pentafluoride, ruthenium acetate, ruthenium octoate, ruthenium hydroxide and the like.

The niobium and ruthenium catalysts are employed in a catalytically effective amount, an amount sufficient to carry out the reaction. This amount can be up to 1.5 weight percent, preferably from 0.01 to 1.0 weight percent, more preferably from 0.06 to 0.6 weight percent based on the total weight of the reactants.

The oxirane compounds which are useful in the process of this invention have the general formula

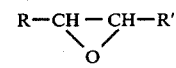

wherein R and R and R' individually are:

(a) hydrogen; or (b) alkyl, linear or branched, saturated or unsaturated, substituted or unsubstitited having from 1 to 8 carbon atoms such as methyl, ethyl, isopropyl hexyl, heptyl, octyl and the like; or (c) aryl, substituted or unsubstituted, having from 6 to 8 carbon atoms such as phenyl, benzyl, phenethyl and the like. Illustrative of such oxirane compounds one can name ethylene oxide, propylene oxide, butylene oxide, styrene oxide and the like. The preferred oxirane are ethylene oxide and propylene oxide.

The monocarboxylic acids useful in the process of this invention have the general formula R"COOH, wherein R" is (a) hydrogen; or (b) alkyl, linear or branched substituted or unsubstituted, saturated or unsaturated having from 1 to 7 carbon atoms such as methyl, ethyl, propyl, acrylyl, methacrylyl, butyl, heptyl and the like; or (c) cycloalkyl, having from 5 to 8 carbon atoms in the molecule, such as cyclopentyl, dimethylcyclopentyl, cyclohexyl, 2-methylcyclohexyl, cyclooctyl and the like; or (d) aryl, substituted or unsubstituted having from six to 8 carbon atoms such as phenyl, benzyl, phenethyl and the like. Illustrative of such carboxylic acids one can name formic acid, acetic acid, monochloroacetic acid, propionic acid, acrylic acid, methacrylic acid, n-butyric acid, octanoic acid, benzoic acid, benzylic acid and the like.

In addition to these monocarboxylic acids certain dicarboxylic acids such as oxalic and succinic acid are useful in the process of this invention.

The preferred carboxylic acids are acrylic acid and methacrylic acid.

The mole ratio of the oxirane compound to the carboxylic acid will vary and will depend on the specific reactants employed. Theoretically the reaction proceeds with one equivalent of oxirane reacting with an equivalent of the carboxyl group. However, if one wishes to produce a polyalkyleneoxy derivative one will use a significant excess of oxirane compound depending upon how many such groups are desired in the molecule. Generally the equivalent ratio of the oxirane groups to carboxylic group will vary from about 1:1 to 10:1 or more.

The reaction mixture may also have present water or an amine such as pyridine, imidazole, benzyltrimethylammonium hydroxide, or other compounds which will act as promoters in the conversion of of the carboxylic acid to the ester. Also, in order to prevent premature polymerization of the ester there may be present in the reaction mixture one or more inhibitors. These inhibitors are well known to those skilled in the art and include hydroquinone, monomethyl ether of hydroquinone, di-tert.-butyl-p-cresol, N,N'-diphenyl-p-phenylenediamine, N,N'-di-1,4-dimethylpentyl-p-phenylenediamine and N,N'-di-beta-naphthyl-p-phenylenediamine.

The reaction need not be conducted in a solvent although the reaction may be conducted in any inert solvent if desired, provided it does not unduly interfere with the desired reaction.

The time of the reaction will vary and will depend upon the specific reactants and the specific reaction conditions, such as temperature, pressure, batch size, etc. It is desirable to have a short a reaction time as practicable in order to minimize the formation of by-products.

The reaction can be carried out at temperature of from about 30° C. to about 300° C., or higher. The greater the reaction temperature the greater is the reaction rate but also the greater is the possibility of formation of unwanted by-products. The optimum reaction temperature for any specific set of reactants will become readily apparent to those skilled in the art and is dependent to an extent upon the particular reactants involved.

The reaction can be carried out at subatmospheric, atmospheric or superatmospheric pressure. The pressure employed is not critical, but it should preferably be above the vapor pressure, at the reaction temperature, of the most volatile component in the reaction mixture in order to maintain a liquid-phase reaction.

In a typical embodiment, propylene oxide and acrylic acid are charged to a reactor together with 0.1 weight percent of niobium pentachloride and heated for a selected period of time. It is then cooled and the desired product recovered by conventional separation and distillation procedures.

The monoesters produced by the process of this invention are the hydroxyalkyl esters of the general formula $$R''-COO-CH-CH-OH$$
$$\phantom{R''-COO-}|\phantom{CH-}|$$
$$\phantom{R''-COO-}R\phantom{CH-}R'$$

wherein R, R' and R" are as defined above. Illustrative of the hydroxyalkyl esters one can mention hydroxyethyl acrylate, hydroxypropyl acrylate, hydroxybutyl acrylate, hydroxyethyl acetate, hydroxypropyl acetate, hydroxyethyl methacrylate, hydroxypropyl methacrylate, hydroxyethyl formate, hydroxyethyl benzoate, hydroxyethyl monocloroacetate, hydroxypropyl dicloroacetate, hydroxypropyl benzoate, and the like.

Of particular interest is the use of the hydroxyalkyl esters of the process of this invention as monomers in the production of photocurable compositions. The most preferred of the hydroxyalkyl esters for use in this capacity are the hydroxyethyl and hydroxypropyl acrylates and methacrylates.

It was an unexpected and unobvious finding that the use of the niobium and ruthenium compounds as catalysts often resulted in a reaction efficiency that was twice that which had heretofore been obtained. Such improvement is of considerable financial benefit and could not have been predicted.

The following examples serve to further illustrate the invention:

EXAMPLE 1

In each of five glass bottles there was charged 72 grams (1.24 moles) of propylene oxide and 72 grams (1.0 moles) of acrylic acid. In each bottle there was added a different catalyst composition. The catalyst was either a niobium or ruthenium salt and was introduced in concentrations based on the total weight of the propylene oxide/acrylic acid mixture. The bottles were sealed and placed in a constant temperature bath maintained at 60° C. for four hours, and then cooled to room temperature. The acrylic acid conversion efficiencies of 2-hydroxypropyl acrylate were determined by gas chromatographic analysis of the crude reaction product and calculated by the formula

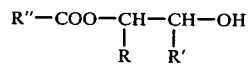

$$EFF. = \frac{\text{Moles of } HPA \text{ prepared}}{\text{Moles of } AA \text{ reacted}} \times 100$$

there was no propylene diacrylate detected. The results are shown in Table I.

For comparative purposes, a glass bottle was charged with 72 grams each of propylene oxide and acrylic acid but no catalyst was added to the mixture. This mixture was then reacted in the same manner as the five catalyst containing mixtures and the results were analyzed using the same method. The result is also shown in Table I.

TABLE I

| Catalyst | Concentration (Weight Percent) | Acrylic Acid Conversion Eff. % | % |
|---|---|---|---|
| Niobium Pentachloride | 0.1 | 51.0 | 65.2 |
| Niobium Pentachloride Water | 0.1 0.1 | 35.4 | 46.7 |
| Niobium Oxalate Water | 0.6 0.24 | 22.8 | 56.3 |
| Niobium Oxalate Water | 0.4 | | |
| Ruthenium Trichloride Hydrate | 0.1 | 58.0 | 57.8 |
| None (Control) | — | 44.2 | 30.8 |

This example establishes the catalytic effect of the niobium and ruthenium compounds and the improvements on efficiency, which range from 1.21 to 2.12 times the efficiency of the control.

EXAMPLE 2

In each of six glass bottles, there were charged 72 grams (1.24 moles) of propylene oxide and 72 grams (1.0) moles of acrylic acid together with the catalyst composition and an organic amine promoter. The catalyst was either niobium oxalate or niobium pentachloride and was introduced in concentrations based on the total weight of the propylene oxide/acrylic acid mixture. The mixtures were then reacted and the results analyzed using conditions and procedures similar to those described in Example 1. Again there was no propylene diacrylate detected. The results are shown in Table II.

For comparative purposes, a mixture similar to that used for comparative purposes in Example 1, was reacted and analyzed along with the six mixtures containing catalysts. The results is shown in Table II.

TABLE II

| Catalyst | Concentration (Weight Percent) | Acrylic Acid Conversion Eff. % | % |
|---|---|---|---|
| Niobium Oxalate | 0.06 | 50.8 | 53.9 |
| Water | 0.24 | | |
| Pyridine | 0.1 | | |
| Niobium Oxalate | 0.1 | 45.4 | 45.1 |
| Water | 0.4 | | |
| Pyridine | 0.1 | | |
| Niobium Pentachloride | 0.1 | 43.6 | 51.3 |
| Pyridine | 0.1 | | |
| Niobium Pentachloride | 0.1 | 51.4 | 45.8 |
| Water | 0.1 | | |
| Pyridine | 0.1 | | |
| Niobium Pentachloride | 0.1 | 49.9 | 59.9 |
| Water | 0.1 | | |
| Imidazole | 0.1 | | |
| Niobium Pentachloride | 0.1 | 71.5 | 80.9 |
| Water | 0.1 | | |
| Benzyltrimethylammonium Hydroxide, 45% in Methanol | 0.1 | | |
| None (Control) | — | 44.4 | 30.6 |

This example illustrates that the presence of organic amines does not hinder and often enhances the catalytic effect of the catalyst shown effective in Example 1. Depending on the catalyst used in the concentration in which it was present, the efficiency of the reaction was increased by a factor of from 1.47 to 2.64 over efficiency achieved in the control run.

EXAMPLE 3

An equimolar mixture of ethylene oxide and acrylic acid was continuously fed to a 400 ml tubular reactor at a rate of 200 ml per hour to give a two-hour residence time. The reactor was maintained at 82° C. by submersion in a electrically heated bath. The feed mixture of ethylene oxide and acrylic acid, of niobium oxalate as a catalyst and 0.1 weight percent of a 40 percent solution of benzyltrimethylammonium hydroxide in methanol. The feed mixtures also contained 0.5 weight percent of N,N'-di-beta-naphthyl-p-phenylenediamine as a polymerization inhibitor. The reaction was maintained at a pressure of 155 psi. The products were analyzed by the methods described in Example 1 and the results indicated a 29.5 percent conversion of of the acrylic acid at a 62.8 percent efficiency to hydroxyethyl acrylate. There was no ethylene diacrylate formed.

What is claimed is:

1. A process for the production of hydroxyalkyl esters of the formula

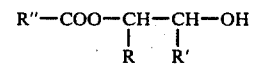

by the reaction of (I) an oxirane compound of the formula

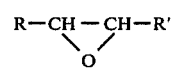

with (II) a carboxylic acid of the formula

wherein R and R' individually are:
(a) hydrogen; or
(b) alkyl, linear or branched, saturated or unsaturated, substituted or unsubstituted, having from 1 to 8 carbon atoms; or
(c) aryl, substituted or unsubstituted, having from 6 to 8 carbon atoms and R" is:
(a) hydrogen; or
(b) alkyl, linear or branched, substituted or unsubstituted, saturated or unsaturated, having from 1 to 7 carbon atoms;
(c) cycloalkyl, having from 5 to 8 carbon atoms in the molecules; or
(d) aryl, substituted or unsubstituted having from 6 to 8 carbon atoms, in contact with a catalytically effective amount sufficient to catalyze the reaction, of a catalyst from the group consisting of the niobium and ruthenium salts of organic or inorganic acids.

2. A process as claimed in claim 1 wherein the said catalyst is niobium pentachloride.

3. A process as claimed in claim 1 wherein the said catalyst is niobium oxalate.

4. A process as claimed in claim 1 wherein the said catalyst is ruthenium trichloride hydrate.

5. A process as claimed in claim 1 wherein the said catalyst is present at a concentration of from 0.01 to 1.0 weight percent based on the total combined weight of components I and II.

6. A process as claimed in claim 1 wherein water is present in the reaction mixture.

7. A process as claimed in claim 1 wherein an organic amine is present in the reaction mixture.

8. A process as claimed in claim 1 wherein component I is propylene oxide.

9. A process as claimed in claim 1 wherein component I is ethylene oxide.

10. A process as claimed in claim 1 wherein component II is acrylic acid.

11. A process as claimed in claim 1 wherein the equivalent ratio of oxirane group of component I to carboxyl group of component II is from 1:1 to 10:1.

* * * * *